US012622579B2

(12) United States Patent
Vinteler et al.

(10) Patent No.: US 12,622,579 B2
(45) Date of Patent: May 12, 2026

(54) MEDICAL DEVICE CLEANING METHOD AND CORRESPONDING CLEANING DEVICE AND CLEANING APPARATUS

(71) Applicant: PLASMABIOTICS, Argenteuil (FR)

(72) Inventors: Daniel Vinteler, Argenteuil (FR); Timothée Durouchoux, Argenteuil (FR)

(73) Assignee: PLASMABIOTICS, Argenteuil (FR)

( * ) Notice: Subject to any disclaimer, the term of this patent is extended or adjusted under 35 U.S.C. 154(b) by 18 days.

(21) Appl. No.: 18/711,299

(22) PCT Filed: Nov. 18, 2022

(86) PCT No.: PCT/EP2022/082499

§ 371 (c)(1),
(2) Date: May 17, 2024

(87) PCT Pub. No.: WO2023/089141

PCT Pub. Date: May 25, 2023

(65) Prior Publication Data

US 2025/0017459 A1      Jan. 16, 2025

(30) Foreign Application Priority Data

Nov. 19, 2021     (EP) .................................... 21306617

(51) Int. Cl.
*A61B 1/12*        (2006.01)
*A61B 90/70*       (2016.01)
(52) U.S. Cl.
CPC .............. *A61B 1/123* (2013.01); *A61B 90/70* (2016.02)

(58) Field of Classification Search
None
See application file for complete search history.

(56) References Cited

U.S. PATENT DOCUMENTS

2009/0229632 A1      9/2009  Labib et al.
2015/0374867 A1      12/2015  Patterson et al.

FOREIGN PATENT DOCUMENTS

EP          0638296  B1     11/1999
JP        2003145064  A  *   5/2003

OTHER PUBLICATIONS

Google Patents translation of EP0638296A1 (Year: 2025).*
Google Patents translation of JP2003145064 (Year: 2025).*
International Search Report issued on Feb. 8, 2023, in corresponding International Patent Application No. PCT/EP2022/082499, 3 pages.

* cited by examiner

*Primary Examiner* — Eric W Golightly
(74) *Attorney, Agent, or Firm* — Maier & Maier, PLLC

(57)          ABSTRACT

A cleaning method for cleaning a surface of a medical device, the method including a contaminant removal phase including: (a) injecting a continuous flow of gas in an atomization chamber, through a first input of the atomization chamber; and (b) introducing a plurality of successive discharges of liquid in the atomization chamber through a second input of the atomization chamber, each discharge including a respective amount of liquid, a duration between two successive discharges being strictly greater than zero, thereby generating, at an output of the atomization chamber, a cleaning flow including, successively over time, liquid droplets suspended in gas, the cleaning flow being oriented towards the surface of the medical device.

17 Claims, 7 Drawing Sheets

MEDICAL DEVICE CLEANING METHOD AND CORRESPONDING CLEANING DEVICE AND CLEANING APPARATUS

FIELD

The present invention relates to a cleaning method for cleaning a surface of a medical device.

The invention applies to cleaning, and more specifically to the removal of contaminant from surfaces of a medical device.

BACKGROUND

The removal of contaminants from surfaces of a medical device, such as an endoscope, is an essential step in the process of cleaning and disinfecting said device, thus ensuring its reusability and preventing cross-contamination.

In the present disclosure, the expression "contaminant" refers to a biofilm and/or to biological soil.

To remove contaminants from a surface of a medical device, such as an endoscope, it is known to expose said medical device to one or several solutions, generally in the form of a jet. Said solutions typically include water, a mix of water and surfactants, or an acidic solution. For instance, to clean a channel of an endoscope (and more generally, to clean an inner surface of a tube included in a medical device), a solution of water and surfactants is circulated through said channel to dislodge the contaminant. This is generally done after a step of brushing: the brushing of the endoscope channels with an appropriate brush diameter is mandatory for channels larger than 1.2 mm, while smaller channels are generally not brushed.

However, such method is not entirely satisfactory.

Indeed, such method relies on the use of brushes, surfactants and other chemicals, which may interact with the medical device and deteriorate it. The use of said chemicals also raises environmental issues, and the brushes produce waste because they are generally single use devices. Moreover, such brushes and chemicals may be costly.

Other methods, such as described in JP 2003 145064, use a continuous liquid flow atomized with a continuous gas flow at a stable pressure. However, such methods are not satisfactory. Indeed, in these methods, a more efficient cleaning is only reached with high pressure which may deteriorate the medical device, and these methods consume a large amount of liquid.

Therefore, a purpose of the invention is to provide a cleaning method that is effective, while being more environment-friendly and cost-effective than known methods, and having a low risk of damaging the medical device.

SUMMARY

To this end, the present invention relates to a method of the aforementioned type, including a contaminant removal phase comprising:

a. injecting a continuous flow of gas in an atomization chamber, through a first input of the atomization chamber;

b. introducing a plurality of successive discharges of liquid in the atomization chamber through a second input of the atomization chamber, each discharge including a respective amount of liquid, a duration between two successive discharges being strictly greater than zero, thereby generating, at an output of the atomization chamber, a cleaning flow comprising, successively over time, liquid droplets suspended in gas, the cleaning flow being oriented towards the surface of the medical device.

Indeed, the introduction of a discharge of liquid in a continuous flow of gas leads to an atomization, i.e., a dispersion, of said liquid into droplets. These droplets are carried away by the flow of gas towards the surface to be cleaned. Due to their small size, the energy transfer from the gas to the droplets is efficient, which allows said droplets to easily remove contaminants from said surface, without the need of additional chemicals. This leads the method according to the disclosure to be environment-friendly.

Furthermore, by injecting several successive discharges of liquid instead of a continuous liquid stream prevents excessive gas pressure drop that would be detrimental to liquid atomization. Indeed, when a discharge of liquid is injected, it blocks the air flow thereby reducing the speed flow of gas, and droplets are created. When the discharge is stopped, the air flow is not blocked anymore so that the speed flow is increased. Increasing the speed flow also leads to the acceleration of the newly created droplets. By successively reducing and increasing the speed flow, the droplets undergo successive accelerations. When arriving at the cleaning surface, the droplets have been highly accelerated. As a result, good cleaning efficiency can be achieved without a need to increase the pressure of the flow of gas to a level that could damage the medical device: for instance, in the case where lumens of endoscope tubes are cleaned, the pressure of the flow of gas can be maintained within a nominal range provided in the specifications of the endoscope. Moreover, the use of such discharges in combination with a continuous flow of gas results in a lower consumption of liquid, that is to say a cost-effective cleaning method.

On the contrary, if a constant flow of droplets is used, as in conventional atomization processes, the pressure of gas tends to drop and the velocity of said droplets is low. This prevents the generation of high shear stress, resulting in a low cleaning efficiency.

By providing a plurality of successive discharges of liquid at a predetermined frequency and with a predetermined duration, the method of the disclosure allows to drastically increase the velocity of the droplets in the flow of gas, generating a sufficient shear stress to achieve an improved cleaning efficiency.

According to other advantageous aspects of the disclosure, the cleaning method includes one or more of the following features, taken alone or in any possible combination:

step b) comprises providing the plurality of successive discharges periodically according to a predetermined frequency and a predetermined duration;

the flow of gas at the output of the atomization chamber, during the contaminant removal phase, is turbulent;

during the contaminant removal phase, a pressure of the gas, at the first input of the atomization chamber, is greater than a pressure of the liquid at the second input of the atomization chamber;

during the contaminant removal phase, a concentration of surfactants in the liquid is lower than 2 mg/L, preferably lower than 200 µg/L, for instance lower than 100 µg/L;

the gas is air, dinitrogen or carbon dioxide;

the cleaning method further includes, prior to the contaminant removal phase, a preliminary phase including providing an initial flow of gas at the output of the atomization chamber, the initial flow of gas at the end of the preliminary phase being turbulent;

the cleaning method further includes, after the contaminant removal phase, a draining phase, including:

outputting, at the output of the atomization chamber, a draining flow of gas; and providing the draining flow of gas to the surface of the medical device to drain residual liquid, the draining flow of gas during the draining phase being turbulent;

the cleaning method further includes, after the contaminant removal phase, a disinfection phase comprising using a washer-disinfector to disinfect the medical device;

the medical device is an endoscope.

The invention also relates to a cleaning device for cleaning a surface of a medical device, the cleaning device comprising:

a gas input and a liquid input, an atomization chamber including a first input, a second input and an output, a gas line fluidly connected between the gas input and the first input of the atomization chamber, a liquid line fluidly connected between the liquid input and the second input of the atomization chamber, a controller configured to control the gas line and the liquid line so that, during a phase of contaminant removal:

a. the gas line allows circulation of gas from the gas input to the first input of the atomization chamber, in order to inject a continuous flow of gas in the atomization chamber through its first input; and b. the liquid line allows circulation of liquid from the liquid input to the second input of the atomization chamber, in order to introduce a plurality of successive discharges of liquid in the atomization chamber through its second input, each discharge including a respective amount of liquid, a duration between two successive discharges being strictly greater than zero, thereby generating, at the output of the atomization chamber, a cleaning flow comprising, successively over time, liquid droplets suspended in gas, the cleaning flow being intended to be oriented towards the surface of the medical device.

According to other advantageous aspects of the disclosure, the cleaning device includes one or more of the following features, taken alone or in any possible combination:

the controller is configured to control the gas line so that the flow of gas at the output of the atomization chamber, during the contaminant removal phase, is turbulent;

the cleaning device further includes a set of electrodes arranged in a path of the flow of gas, the controller being configured to control a voltage between the electrodes to a level suitable for ionizing the flow of gas.

The invention also relates to a cleaning assembly including a cleaning device as described above, the cleaning assembly further comprising a liquid supply fluidly connected to the liquid input of the cleaning device, and a gas supply fluidly connected to the gas input of the cleaning device.

The invention also relates to a washer-disinfector including a cleaning device as described above.

DETAILED DESCRIPTION

Figure 1:
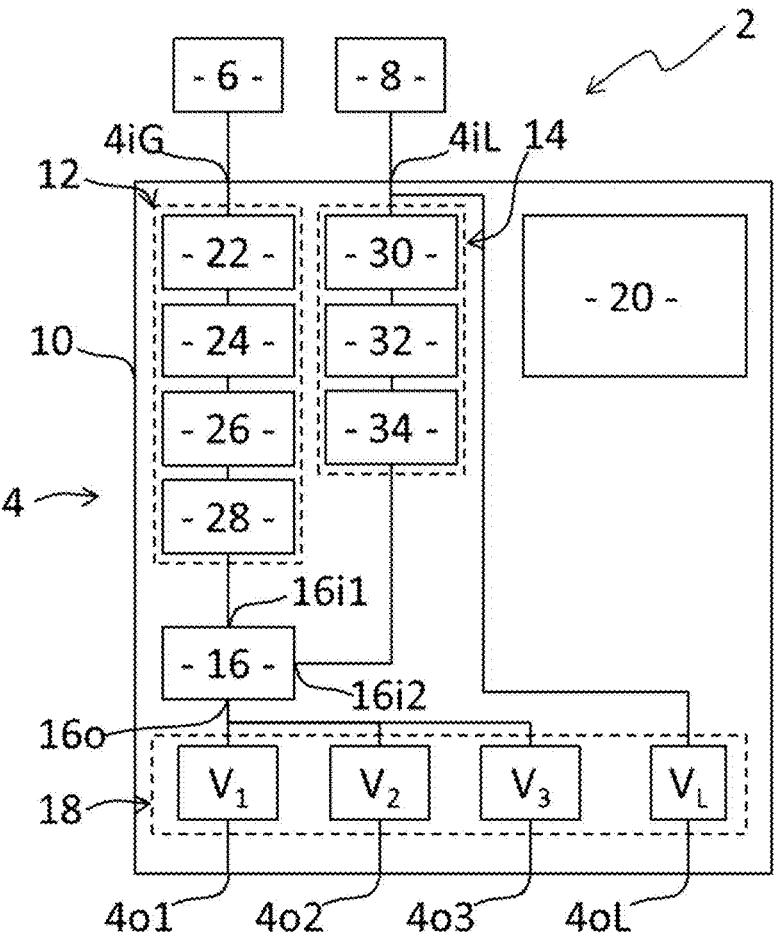
FIG. 1 is a schematic representation of a first embodiment of a cleaning assembly according to the disclosure.

A cleaning assembly 2 according to the disclosure is shown on FIG. 1.

The cleaning assembly comprises a cleaning device 4, a gas supply 6 and a liquid supply 8.

The cleaning device 4 is configured to receive gas and liquid from the gas supply 6 and the liquid supply 8 respectively, and to output at least one flow of gas and/or liquid that is suitable for cleaning surfaces of a medical device.

In the context of the disclosure, the expression "cleaning" refers to the removal of contaminants from surfaces of the medical device. Moreover, as stated previously, the expression "contaminant" refers to a biofilm and/or to biological soil.

The medical device is, for instance, an endoscope, a transesophageal (TEE) probe, an endocavitary probe, and the like. Furthermore, the surfaces of the medical device that are to be cleaned by the medical assembly 2 may be internal surfaces (such as lumens of tubes of the medical device) or external surfaces (such as an outer wall, or a surface of a lens).

Gas and Liquid Supplies

The gas supply 6 is fluidly connected to a gas input 4$i$G of the cleaning device 4 to provide gas. Furthermore, the liquid supply 8 is fluidly connected to a liquid input 4$i$L of the cleaning device 4.

Preferably, neither the gas supply 6 nor the liquid supply 8 is integral with the cleaning device 4. In this case, the connection of the gas supply 6, respectively the liquid supply 8, to the cleaning device 4 is reversible. Therefore, the cleaning device 4 can be detached from the gas supply 6, respectively the liquid supply 8, for connection to another gas supply, respectively another liquid supply, and/or to allow relocation of the cleaning device 4.

The gas supply 6 is, for instance, a gas piping installation or a gas bottle.

Preferably, the gas provided by the gas supply 6 is air, dinitrogen or carbon dioxide.

Preferably, the gas flow rate is comprised between 10 L/min and 100 L/min, preferably between 40 L/min and 80 L/min. The flowrate is depending on the surface area to be cleaned. Indeed, the larger the surface to be cleaned, the higher the flowrate needed to reach an efficient cleaning. In the same manner, if the number of surfaces to clean simultaneously is high, e.g. in case of multiple channels of endoscope to clean simultaneously, the flowrate needed to reach an efficient cleaning is high.

Furthermore, the liquid supply 8 is, for instance, a liquid supply network (such as a water supply network) or a liquid tank.

Preferably, the liquid provided by the liquid supply 8 is water. For instance, said water is osmosed water, distilled water, or deionized water, or type II laboratory grade purified water or similar.

As an example, the liquid provided by the liquid supply 8 is drinking water, preferably liquid water compliant with one or more of: the European Drinking Water Directive published by the European Union, the Safe Drinking Water Act published by the United States Environmental Protection Agency, standard GB3838-2002 (Type II) published by the Chinese Ministry of Environmental Protection, and the guidelines relative to drinking water published by the World Health Organization.

Advantageously, the liquid supply 8 is configured so that a concentration of surfactants in the liquid is lower than 2 mg/L, preferably lower than 200 µg/L, for instance lower that 100 µg/L. Indeed, as will be shown later, the cleaning device 4 is configured so that efficient cleaning is achieved without resorting to surfactants or other chemical agents. The value of 2 mg/L corresponds to a maximum value for total organic carbon in drinking water that is recommended by, for instance, European regulations. A maximum concentration value for surfactants alone is generally lower than such value, and values lower than 200 µg/L, for instance lower that 100 µg/L, are believed to be safe for the environment. With such values, the effect of surfactants on cleaning efficiency is negligible.

Cleaning Device 4

As shown on FIG. 1, the cleaning device 4 comprises an enclosure 10 which houses a gas line 12, a liquid line 14, an atomization chamber 16, an output stage 18 and a controller 20.

Gas Line 12

The gas line 12 is fluidly connected to a first input 16i1 of the atomization chamber 16. Moreover, the liquid line 14 is fluidly connected to a second input 16i2 of the atomization chamber 16. Furthermore, the output stage 18 is fluidly connected to an output 16o of the atomization chamber 16. Finally, the controller 20 is configured to control each of the gas line 12, the liquid line 14, and the output stage 18.

The gas line 12 is configured to provide a flow of gas having predetermined properties (such as flow speed, pressure and/or duration) to the atomization chamber 16. In other words, the gas line 12 is configured to adjust the properties of the gas provided by the gas supply 6, based on controls of the controller 20 representative of current desired properties of the flow of gas to be injected at the first input 16i1 of the atomization chamber 16.

Preferably, the gas line 12 comprises a gas regulator 22, a flowmeter 24, a proportioning valve 26 and a check valve 28 connected in series.

The input of the gas regulator 22 is connected to the gas input 4iG of the cleaning device 4. The gas regulator 22 is configured to lower the pressure of the gas received at the gas input 4iG to a predetermined gas pressure. For instance, the predetermined gas pressure is between 2 bar and 4 bar, preferably 3 bar, whereas the pressure of the gas at the gas input 4iG can reach up to 10 bar. As a result, the gas regulator 22 helps protecting the elements that are located downstream with respect to the gas flow, by lowering the pressure of the gas at the gas input 4iG, therefore preventing degradation of said elements.

Moreover, the flowmeter 24 is configured to provide, to the controller 20, a flow measurement of the gas output by the gas regulator 22. This provides an undirect measurement of the gas pressure at an input of the proportioning valve 26, since the design parameters of the cleaning device 4 (such as diameters of the pipes through which the gas flows, inside the cleaning device 4) are known, thereby allowing control of the proportioning valve 26.

Alternatively, or in addition, a gas pressure sensor (not shown) is provided between the gas regulator 22 and the proportioning valve 26 to provide a direct measurement of the gas pressure at the input of the proportioning valve 26, thereby allowing control of the gas line 12 based on such pressure measurement.

Furthermore, the proportioning valve 26 is configured to adjust the flow of the gas received from the flowmeter 24 to a target flow (i.e., to a target gas pressure, since flow and pressure are related), based on a control received from the controller 20. Such proportioning valve is, for instance, a solenoid valve.

Finally, the check valve 28 is configured to prevent flow of fluids in a direction from the atomization chamber 16 to the gas line 12, while allowing flow of gas from the proportioning valve 26 to the atomization chamber 16. The output of the check valve 28 is connected to the first input 16i1 of the atomization chamber 16.

Liquid Line 14

The liquid line 14 is configured to provide a flow of liquid having predetermined properties (such as flow speed, pressure and/or duration) to the atomization chamber 16. In other words, the liquid line 14 is configured to adjust the properties of the liquid provided by the liquid supply 8, based on controls of the controller 20 representative of current desired properties of the flow of liquid to be injected at the second input 16i2 of the atomization chamber 16.

Preferably, the liquid line 14 comprises a liquid regulator 30, a controllable valve 32 and a liquid check valve 34 fluidly connected in series, in this order.

The liquid regulator 30 is configured to lower the pressure of the liquid received from the liquid supply 8 at the liquid input 4iL to a predetermined liquid pressure. As a result, the liquid regulator 30 helps protecting the elements that are located downstream with respect to the liquid flow, by lowering the pressure of the liquid that is available at the liquid input 4iL. For instance, the predetermined liquid pressure is between 1 bar and 4 bar, preferably between 2 bar and 3 bar.

The controllable valve 32, which can have an open state and a closed state, is configured to selectively allow or prevent flowing of liquid from the liquid supply 8 to the atomization chamber 16, depending on controls received from the controller 20, in order to deliver a predefined amount of liquid (hereinafter, "discharge") to the atomization chamber 16.

Furthermore, the liquid check valve 34 is configured to prevent flow of fluids in a direction from the atomization chamber 16 to the liquid line 14, while allowing flow of liquid from the controllable valve 32 to the atomization chamber 16. The output of the liquid check valve 34 is fluidly connected to the second input 16i2 of the atomization chamber 16.

Atomization Chamber 16

The atomization chamber 16 is configured to mix the gas flow and the discharges injected at the first and second inputs 16i1, 16i2 respectively, and to provide, at its output 16o, a flow comprising at least gas (depending on whether the valve 32 is closed or open). More precisely, when provided with gas flow and discharges of liquid with suitable flow and/or pressure, the atomization chamber 16 is configured to provide, at its output 16o, a cleaning flow comprising liquid droplets suspended in a flow of gas. Since the liquid discharges are injected in a discontinuous manner, the cleaning flow available at the output 16o successively comprises gas without droplets and gas including liquid droplets in suspension therein.

Preferably, the atomization chamber 16 forms a T-connection.

Alternatively, the atomization chamber 16 includes several outputs. In this case, each output is connected to a respective valve $V_i$ (described below) of the output stage 18.

Output Stage 18

The output stage 18 includes at least one valve, such as N valves $V_1$ to $V_N$, N being an integer strictly greater than 0. Each valve has an input that is fluidly connected to the output 16o of the atomization chamber 16, and an output that is fluidly connected to a respective outlet of the cleaning device 4. As a result, flow of fluid(s) from the atomization chamber 16 to the outlet(s) of the cleaning device 4 can be selectively allowed or prevented, depending on a state of each valve (controlled by the controller 20 or an operator).

For instance, in the example of FIG. 1, the output stage 18 includes three valves $V_1$, $V_2$, $V_3$, each having its input fluidly connected to the output 16o of the atomization chamber 16, and its output fluidly connected to an outlet 4o1, 4o2, 4o3 of the cleaning device 4 respectively.

Preferably, a pressure sensor is provided at the output of each valve $V_i$. This is advantageous, as the controller 20 may be configured to provide alerts based on such pressure measurements. For instance, the controller may be configured to generate an alert indicating that the measured pressure is lower than a predetermined threshold pressure, which may be due to a malfunction in the cleaning device 4.

Alternatively, in the case where the atomization chamber 16 includes several outputs, the input of each valve of the output stage 18 is fluidly connected to a respective output of the plurality of outputs of the atomization chamber 16.

Optionally, the output stage 18 includes a liquid valve $V_L$ that is directly fluidly connected between the liquid input 4iL of the cleaning device 4 and a corresponding liquid outlet 4oL of the cleaning device 4. As a result, depending on a closed or open state (controlled by the controller 20 or an operator) of the liquid valve $V_L$, a flow of pressurized liquid can be provided at the liquid outlet of the cleaning device 4.

This feature is advantageous, because such liquid outlet 4oL gives access to liquid at a relatively high pressure, thereby allowing an operator to perform, for instance, preliminary cleaning of external surfaces of the medical device, for example by using a dedicated nozzle.

Controller 20

As stated previously, the controller 20 is configured to control each of the gas line 12 and the liquid line 14.

More precisely, the controller 20 is configured to control the gas line 12, during a contaminant removal phase, in order to inject a continuous flow of gas in the atomization chamber 16, through the first input 16i1 of said atomization chamber 16.

The controller 20 is further configured to control the liquid line 14, during said contaminant removal phase, in order to introduce (i.e., to deliver) a plurality of successive discharges of liquid in the atomization chamber 16 through its second input 16i2. More precisely, each discharge includes a respective amount of liquid, which is predetermined. For instance, the amount of liquid depends on the surface of the medical device that is currently cleaned.

Furthermore, the controller 20 is configured to control the liquid line 14, during said contaminant removal phase, so that a duration between two successive discharges is strictly greater than zero. In other words, the controller 20 is configured to control the controllable valve 32 so that is successively closes over time.

Preferably, the controller 20 is configured to control the liquid line 14 so that, during the contaminant removal phase, the successive discharges are provided periodically to the second input 16i2 of the atomization chamber 16, according to a predetermined frequency and a predetermined duration.

Advantageously, the controller 20 is configured to control the gas line 12, during the contaminant removal phase, so that the flow of gas at the output 16o of the atomization chamber 16 is turbulent. This is advantageous because a turbulent flow of said gas favors atomization of the liquid into droplets, which enhances cleaning efficiency. Moreover, such turbulent gas flow provides radial and tangential speed components to said droplets (with respect to a longitudinal direction of the flow at each outlet 4o1-4o3), further enhancing cleaning efficiency.

By "turbulent flow", it is meant, in the context of the disclosure, a flow having a Reynolds number higher than 2300.

Even more advantageously, the controller 20 is configured to control the gas line 12 and/or the liquid line 14, during the contaminant removal phase, so that a pressure of the gas, at the output 16o of the atomization chamber 16, is greater than a pressure of the liquid. Such feature further promotes atomization of the liquid into droplets.

Preferably, the controller 20 is further configured to control the gas line 12 and the liquid line 14 so that, during a preliminary phase prior to the contaminant removal phase, an initial flow of gas is provided at the output 16o of the atomization chamber 16, the initial flow of gas at the end of the preliminary phase being turbulent. In other words, the controller 20 is configured to control the controllable valve 32 so that it remains closed during said preliminary phase. Furthermore, the controller 20 is configured to control the gas line 12 so that the initial flow of gas is turbulent at least at the end of the preliminary phase.

Such preliminary phase allows to remove debris and clumps of organic material, if any are present on the surface to be cleaned.

Preferably, the controller 20 is further configured to control the gas line 12, during a draining phase after the contaminant removal phase, so that a turbulent draining flow of gas is provided at the output 16o of the atomization chamber 16. In other words, the controller 20 is configured to control the controllable valve 32 so that it remains closed during said draining phase. Such draining phase is advantageous, as it allows blowing residual liquid that may remain on the cleaned surface, thereby allowing a quicker drying.

Operation

Figure 2:
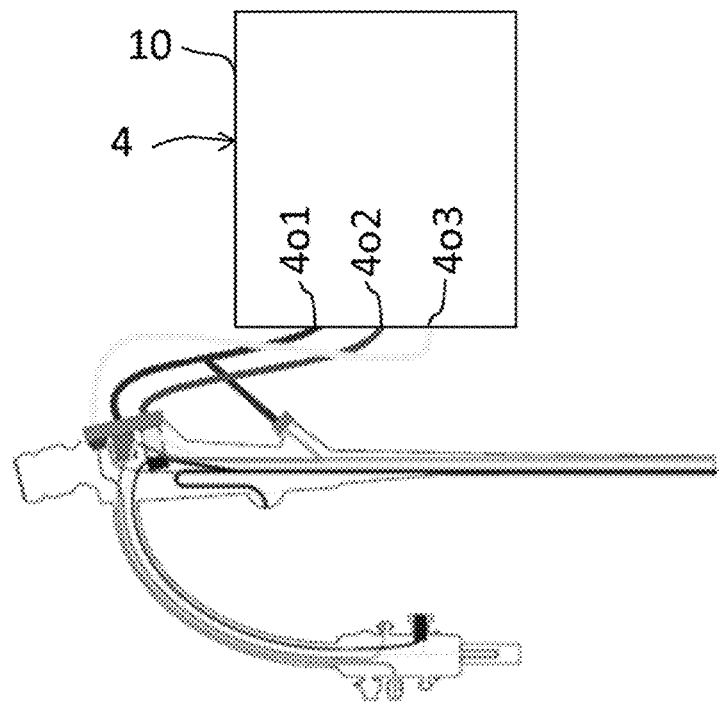
FIG. 2 is a schematic representation of a medical device connected to a cleaning device of the cleaning assembly of FIG. 1.
Figure 3:
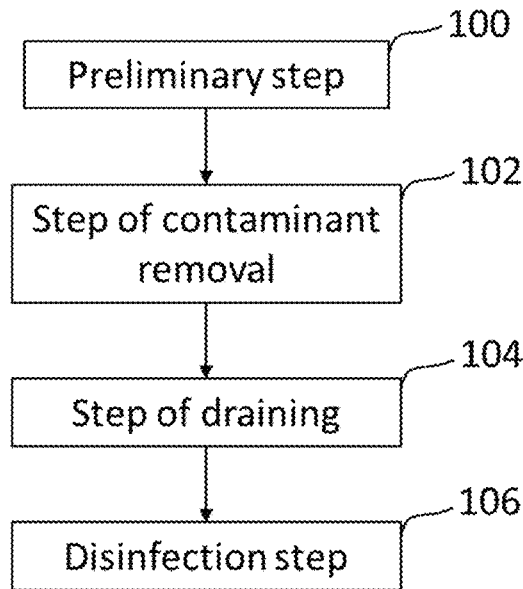
FIG. 3 is a flowchart of a cleaning method implemented using the cleaning assembly of FIG. 1.

Operation of the cleaning assembly 2 will now be described with reference to FIGS. 2-4.

First, the inputs 4*i*G and 4*i*L of the cleaning device 4 are respectively connected to a gas supply 6 and a liquid supply 8.

Then, the medical device is provided, and at least part (hereinafter, "active outlets") of the outlets 4*o*1-4*o*N of the cleaning device 4 are oriented toward corresponding surfaces to be cleaned of the medical device. For instance, if the medical device is an endoscope, at least part of the channels of the endoscope are connected to respective outlets of the cleaning device 4 (example on FIG. 2).

Then, during an optional preliminary phase 100, the controller 20 controls the gas line 12 and the liquid line 14 so that an initial flow of gas is provided at the output 16*o* of the atomization chamber 16. More precisely, the controller 20 controls the gas line 12 so that the initial flow of gas at the end of the preliminary phase 100 is turbulent. Furthermore, during the preliminary phase 100, the controller 20 controls each valve associated to an active outlet so that is in an open state, thereby allowing gas flow from the output 16*o* of the atomization chamber 16 to each active outlet.

Figure 4:
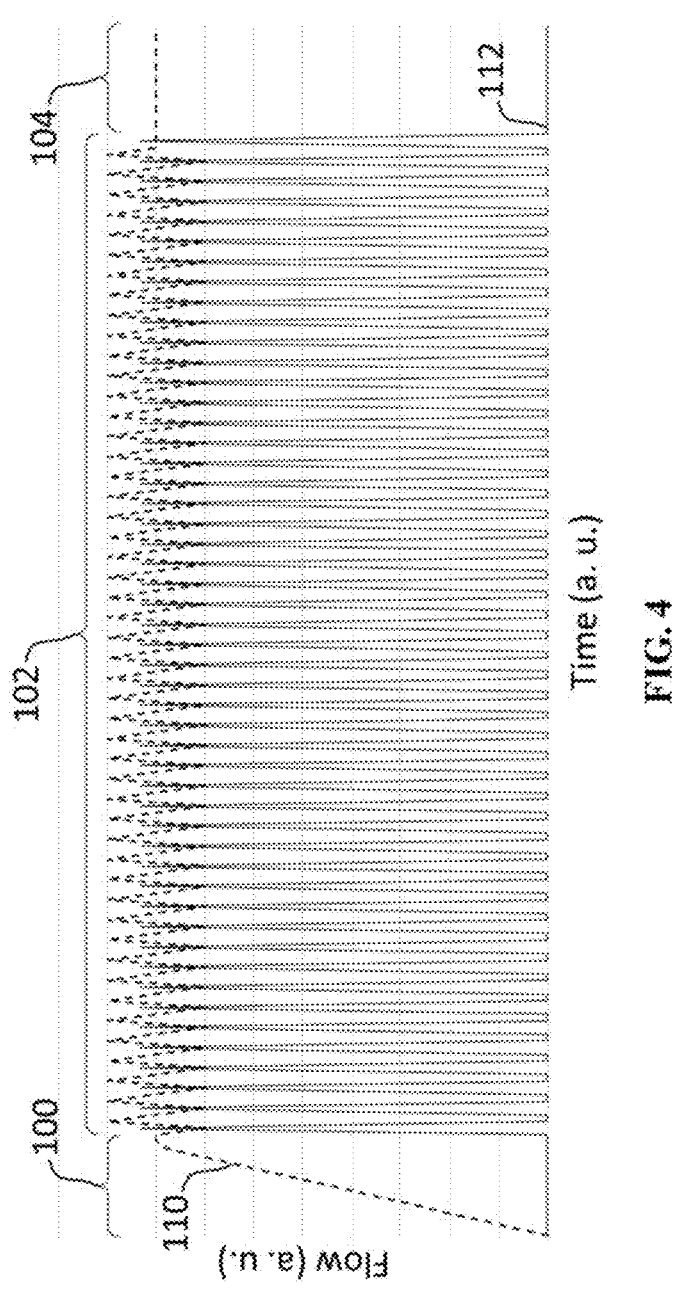
FIG. 4 is a graph showing a temporal evolution of the flows of gas and liquid provided, over time, to an atomization chamber of the cleaning assembly of FIG. 1.

As shown on FIG. 4, during the preliminary phase 100, the flow of gas (dashed line 110) at the first input 16*i*1 of the atomization chamber 16 rises, while the flow of liquid (solid line 112) at the second input 16*i*2 of the atomization chamber 16 stays equal to 0 (no liquid flow).

On FIG. 4, lines 110 and 112 (which respectively represent the flow of gas and the flow of liquid at corresponding inputs of the atomization chamber 16) are represented on different scales.

The optional preliminary phase 100 is performed prior to a contaminant removal phase 102.

During the contaminant removal phase 102, the controller 20 controls each of the gas line 12 and the liquid line 14 so that:

a continuous flow of gas is injected in the atomization chamber 16, through the first input 16*i*1; and a plurality of successive discharges of liquid are introduced in the atomization chamber 16 through the second input 16*i*2.

On FIG. 4, the introduction of said discharges in the atomization chamber 16 corresponds to the successive peaks of the solid line 112.

As stated previously, each discharge includes a respective amount of liquid. The amount of liquid per discharge is ranging from 60 cm³/minute to 600 cm³/minute, preferably from 300 cm³/minute to 600 cm³/minute. An amount of liquid above 600 cm³/minute prevents a sufficient acceleration of the droplets, resulting in a less efficient cleaning of the surface. Furthermore, a duration between two successive discharges is strictly greater than zero.

Preferably, the duration of each discharge is comprised between 0.1 second and 10 seconds, with a frequency comprised between 1 and 1000 discharges per minute, for instance between 3 and 300 discharges per minute. More preferably, the duration of each discharge is comprised between 0.1 second and 5 seconds, most preferably between 0.5 second and 2.5 seconds. More preferably, the frequency is comprised between 1 discharge per minute and 50 discharges per minute, most preferably between 2 discharges per minute and 25 discharges per minute. For example, a frequency of 20 discharges of liquid per minute refers to a discharge of liquid starting each 3 seconds. By providing successive discharges of liquid at this frequency range and with this duration range, the method of the disclosure allows to drastically increase the velocity of the droplets in the flow of gas, generating a sufficient shear stress to achieve an improved cleaning efficiency. Indeed, if the quantity of liquid provided in a discharge (depending on the flowrate and the duration of the discharge) is too large, the velocity of the droplets cannot be sufficiently increased, resulting a decay of the cleaning efficiency. On the contrary, if the quantity of liquid provided in a discharge is too low, the optimal cleaning efficiency is not achieved as the impact velocity of the droplets on the surface is too low. The duration and frequency of discharge of this disclosure allows to create droplets with an optimal size and an optimal increase of the velocity of said droplets so that a required shear stress is achieved.

The frequency and duration of the discharge may also be expressed as a ratio between the duration of a discharge and the duration between the end of the discharge and the time of the beginning of the next discharge. For example, for a frequency of 2 discharges per minute and a duration of the discharge of 10 seconds, the duration between the end of the discharge and the time of the beginning of the next discharge is 20 seconds leading to a ratio of 1:2. In other words, a ratio of 1:2 means that 1 sequence of time, for example 10s, of liquid and gas injection (wherein droplets are discharged in a flow of gas) is followed by 2 sequences of time, for example 20s, of gas alone, thus in one minute, there would be two discharges of liquid, each discharges lasting for 10 seconds. Moreover, a total duration of the contaminant removal phase 102 is preferably comprised between 60 seconds and 600 seconds. Such parameters are advantageous, since they allow an atomization of the liquid discharges into droplets, therefore leading to a satisfying cleaning efficiency, while minimizing the quantity of liquid used for cleaning.

Preferably, the duty cycle is ranging from 10% to 50%, preferably from 20% to 40%. The duty cycle refers to the percentage of the ratio of discharge duration to the total period of a cleaning cycle, i.e. the cycle defined by a discharge followed by a flow of gas alone. The total period of a cleaning cycle corresponds to the sum of the duration of a discharge and the duration of a flow of gas alone, in other words, it corresponds to the duration between the start of a discharge and the start of the next discharge.

During such the contaminant removal phase 102, the output of the atomization chamber 16 is directed towards the surface(s) of the medical device that are to be cleaned.

Preferably, during the contaminant removal phase 102, the flow of gas at the output of the atomization chamber 16 is turbulent. For instance, this is achieved with the following parameters: gas flow rate comprised between 10 L/min and 100 L/min, preferably between 40 L/min and 80 L/min, and tubing diameter comprised between 1 mm and 10 mm. These parameters result in a Reynolds number between 3500 and 100000, depending on the amount of liquid injected in the atomization chamber 16. This corresponds to a turbulent flow.

Furthermore, a pressure of the gas, at the first input 16*i*1 of the atomization chamber 16, is preferably greater than a pressure of the liquid at the second input 16*i*2 of the atomization chamber 16.

Advantageously, during the contaminant removal phase 102, the plurality of successive discharges are provided periodically at the second input 16*i*2 of the atomization chamber 16, according to a predetermined frequency and a predetermined duration.

After the contaminant removal phase 102, an optional draining phase 104 may be performed. During such draining phase 104, the controller 20 controls the gas line 12 and the liquid line 14 so that a draining flow of gas (without liquid) is provided at the output of the atomization chamber 16. The controller 20 further controls the valves $V_1$-$V_N$ so that the draining flow of gas is provided to the surface(s) of the medical device. This allows draining of residual liquid. Furthermore, during the draining phase 104, the draining flow of gas is turbulent.

As shown on FIG. 4, during the draining phase 104, the flow of liquid 112 at the second input 16*i*2 of the atomization chamber 16 is equal to 0 (no liquid flow), while the flow of gas 110 at the first input 16*i*1 of the atomization chamber 16 is strictly higher than 0.

Then, during an optional disinfection phase 106, which may occur after the contaminant removal phase 102 or the optional draining phase 104, the medical device is arranged in a washer-disinfector and is disinfected.

Results

The cleaning results of the cleaning method according to the disclosure will now be described, with reference to FIG. 5. The duty cycle used in FIG. 5 is 33%.

A 150 cm length polytetrafluorethylene tube was contaminated by a bacterial biofilm. More precisely, a nutrient broth was circulated through the tube to cause biofilm formation, which was then inoculated with bacteria (*Pseudomonas aeruginosa* CIP A22) and incubated. Moreover, soil (as described in norm ISO 15883-5 Annex I, also called "German soil") was mechanically introduced in the tube using a syringe.

A section of this tubing was then inserted in a surrogate device according to norm ISO 15883-4 Annex H block B2, and submitted to the cleaning method according to the disclosure. Biofilm and soil protein concentration was then measured at various locations along said tubing.

Figure 5A:
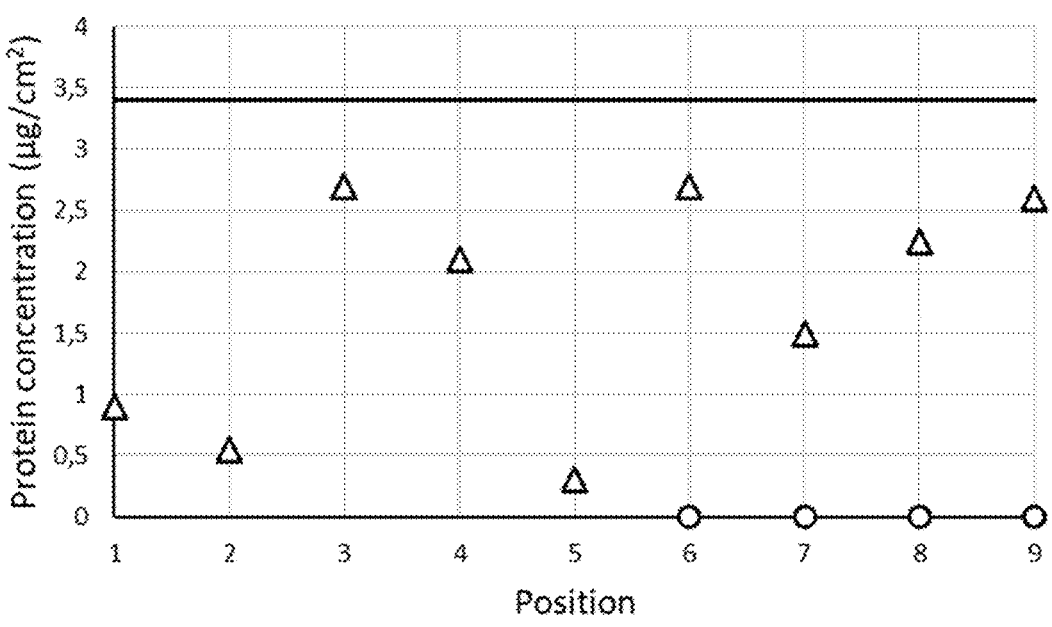
FIG. 5A, respectively

As can be seen on FIG. 5A, at every measurement location, the soil protein concentration (triangles) is, at most, equal to 2.7 $\mu g/cm^2$, the alert level being set to 3.4 $\mu g/cm^2$.

Moreover, for every available measurement location, the biofilm protein concentration (circles) is, equal to 0 $\mu g/cm^2$, the alert level being set to 3.4 $\mu g/cm^2$.

Figure 5B:
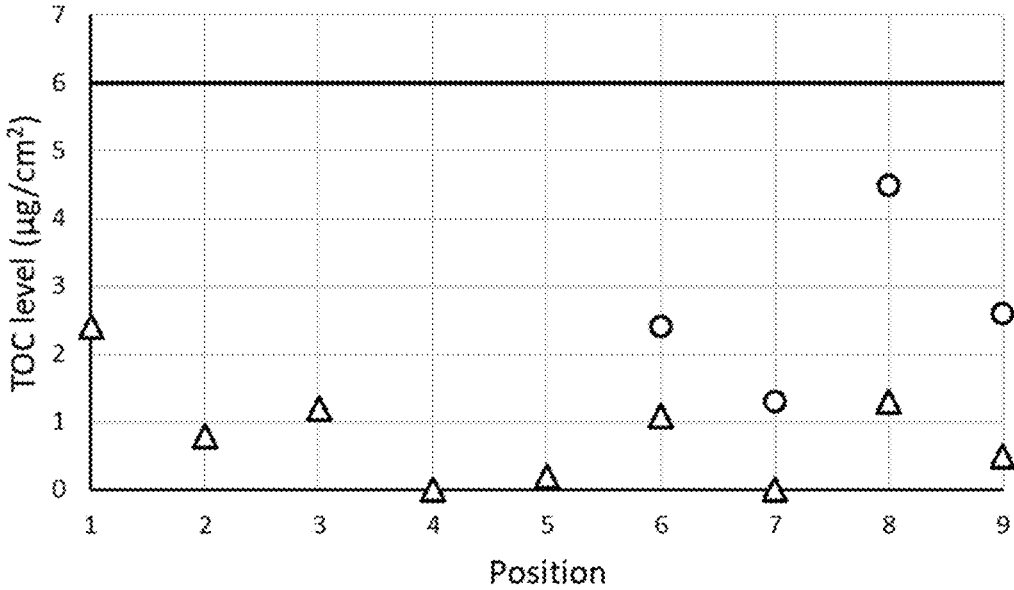
FIG. 5B, is a graph showing protein concentration, respectively total organic carbon level, for both biofilm and soil, at several measurement locations along a tube that has been cleaned using the cleaning assembly of FIG. 1.

As can be seen on FIG. 5B, at every measurement location, the total organic carbon level for soil (triangles) is, at most, equal to 2.4 $\mu g/cm^2$, the alert level being set to 6 $\mu g/cm^2$.

Moreover, for every available measurement location, the total organic carbon level for biofilm (circles) is, at most, equal to 4.5 $\mu g/cm^2$, the alert level being set to 6 $\mu g/cm^2$.

Therefore, the cleaning method according to the disclosure provides cleaning results that are compliant with the limits that have been set. In other words, the cleaning method according to the disclosure provides excellent cleaning results, without using surfactants or any other chemical agent.

In another example, the efficiency of the cleaning is measured for several values of gas and liquid pressures and several predetermined frequencies of successive discharges.

In this example, only soil ("German soil") was mechanically introduced in the tube using a syringe.

Then, the tube was submitted to the cleaning method of the disclosure. In a first test, the cleaning method uses a continuous flow of gas (air) characterized by a pressure comprised between 0 and 1 bar (FIG. 7A). In a second test, the cleaning method uses a continuous flow of gas characterized by a pressure comprised between 2 and 7 bar (FIG. 7B). For each of the first or second test, a liquid (water) is introduced with a pressure comprised between 0 and 4 bars. The liquid is introduced in the form of a plurality of discharges using the following ratio:

1 sequence of time of liquid and gas followed by 1 sequence of time of gas alone (1:1), 1 sequence of time of liquid and gas followed by 2 sequences of time of gas alone (1:2), 2 sequences of time of liquid and gas followed by 1 sequence of time of gas alone (2:1), 2 sequences of time of liquid and gas followed by 3 sequences of time of gas alone (2:3), or 3 sequences of time of liquid and gas followed by 2 sequences of time of gas alone (3:2).

For each ratio, the pressure of the liquid is maintained constant.

The cleaning is measured using three criteria: (i) visual check, (ii) the amount of residual soil proteins and (iii) the amount of residual Total Organic Carbon. The cleaning is efficiently performed if the surface is visually clean, the measured residual soil proteins is inferior to 6.4 $\mu g/cm^2$ and the measured TOC is inferior to 12 $\mu g/cm^2$.

For both the first and second tests, the efficiency of the cleaning using the method of the disclosure is compared to the efficiency of cleaning using the known method of cleaning using a continuous flow of liquid (C) instead of successive discharges.

Figure 7:
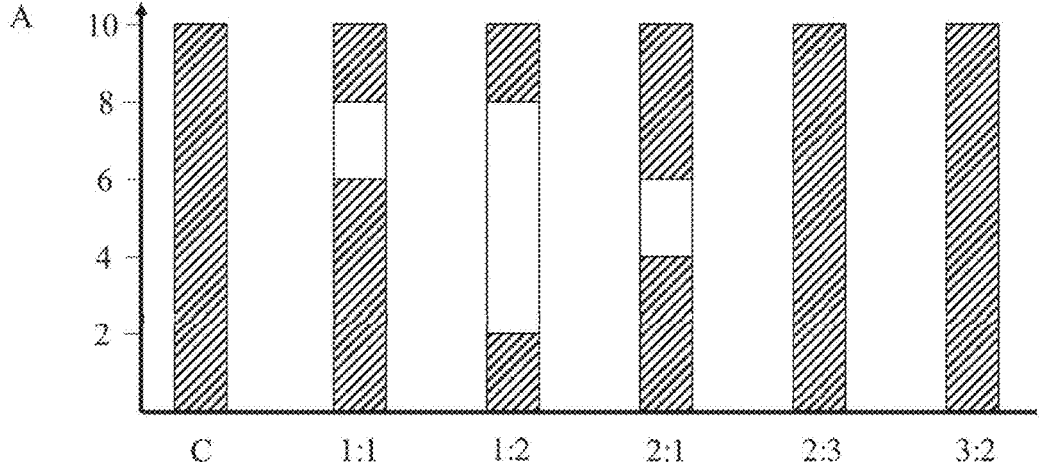
FIG. 7A, respectively
FIG. 7B, is a graph showing the cleaning efficiency considering pressure of gas lower and larger than 1 bar respectively (comprised between 0 and 1 bar, or comprised between 2 and 7 bars) and several values of pressure of liquid and discharge ratio.
Figure 7:
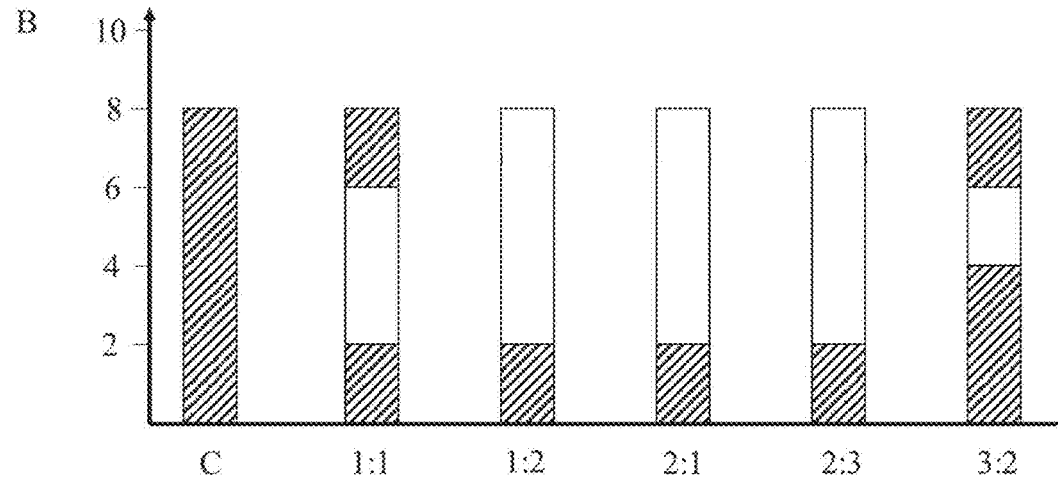

The cleaning results of this example are shown in FIG. 7. FIG. 7A shows the first test wherein the continuous flow of gas is characterized by a pressure comprised between 0 and 1 bar whereas FIG. 7B shows the second test wherein the continuous flow of gas is characterized by a pressure comprised between 2 and 7 bar. For a continuous flow of gas characterized by a pressure larger than 7 bar, the cleaning is always inefficient and even leads to a deterioration of the medical device.

Each bar represents the cleaning efficiency for one ratio (1:1, 1:2, 2:1, 2:3, or 3:2). The left-hand side bar represents the cleaning efficiency for the continuous flow of liquid (C). The shaded part of the bars represents the range of the liquid pressure leading to an inefficient cleaning. For each of the first and second test, the cleaning using the known method is inefficient. Considering the cleaning method of the disclosure, the cleaning is efficient on a larger range of liquid pressure when using a continuous flow of gas with a pressure comprised between 2 and 7 bar. But this result also shows that even when using a low gas pressure (lower than 1 bar; FIG. 7A) and using a ratio of 1 sequence of time of liquid and gas followed by 2 sequences of time of gas alone, the cleaning is efficient even for a low liquid pressure (around 3 bars) thereby avoiding any damage to the medical device. This low liquid pressure can also be efficiently used when using a flow of gas with a pressure comprised between 2 and 7 bar for several ratio.

In a last example, it has been found that the efficient cleaning parameters are different according to the family of endoscope. Indeed, the norm ISO 15883-4 Annex H defines several families of endoscopes depending of the configuration of the tubes. When considering three channels (C1, C2 and C3) of the endoscope which merge inside the scope into one tube, three outlets 4*o*1-4*o*3 of the cleaning devices 4 may be respectively connected to the channels of the endoscope as represented in FIG. 2. In order to efficiently clean each channel, the method of the disclosure may comprise three cleaning modes (F1, F2, F3) that are preferably performed successively. Each cleaning mode comprises at least one cleaning cycle. For example, each cleaning cycle comprises between 10 and 20 discharge periods. For the three cleaning modes (i.e., during the whole application of the method of the disclosure), the gas pressure, liquid pressure and discharge duration are the same. The first cleaning mode F1 comprises three cleaning cycles, each cleaning cycle allowing to clean one of the three channels (C1, C2 and C3). The three cleaning cycles are performed successively by successively opening and closing the valves $V_1$, $V_2$ and $V_3$ of the outlets 4o1-4o3. The second cleaning mode F2 comprises one cleaning cycle allowing to clean the second channel C2. Finally, the third cleaning mode comprises two cleaning cycles performed successively. The first cleaning cycle allows to clean simultaneously the channels C1 and C2 by simultaneously opening the valves $V_1$ and $V_2$ of the outlets 4o1-4o2. Then the second cleaning cycle allows to clean simultaneously the channels C2 and C3 by simultaneously opening the valves $V_2$ and $V_3$ of the outlets 4o2-4o3. The successive application of these three cleaning modes allows to efficiently clean the overall families of endoscopes defined in the norm ISO 15883-4 Annex H.

In another example, the cleaning efficiency of the method of the disclosure is compared to the cleaning efficiency of a known method which involves a continuous flow of liquid. The method of the disclosure uses a duty cycle of 33% (1 sequence of time of liquid and gas followed by 2 sequences of time of gas alone). The cleaning has been performed on a three-channels (C1, C2 and C3) endoscope described in the norm ISO 15883-4 Annex H.

Figure 8:
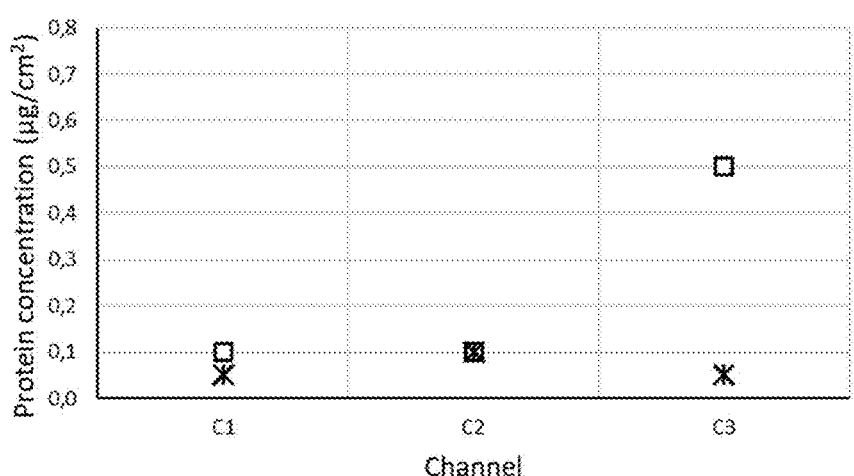
FIG. 8 is a graph showing the cleaning efficiency of the method of the disclosure compared to a known method.

The results are shown in FIG. 8 representing the protein concentration in g/cm$^2$ in each of the channels C1-C3. The alert level, corresponding to the maximum acceptable threshold for protein concentration at the surface, is set to 3.1 μg/cm$^2$. As can be seen in this figure, in every channel C1-C3, the protein concentration resulting from a cleaning according to the method of the disclosure, represented by the asterisks, is, at most, equal to 0.1 μg/cm$^2$, way below the alert level. Moreover, the protein concentration reached by the method of the disclosure is always lower or equal and is up to 10 times smaller than the concentration reached by the known method represented by the squares.

Finally, in a last example, the cleaning efficiency of the method of the disclosure is compared for the three families of endoscopes described in the norm ISO 15883-4 Annex H. The first family corresponds to endoscopes having 3 channels (FIG. 9A), the second family corresponds to endoscopes having 4 channels (FIG. 9B) and the third family corresponds to endoscopes having 2 channels (FIG. 9C). The method uses a duty cycle of 33%.

Figure 9A:
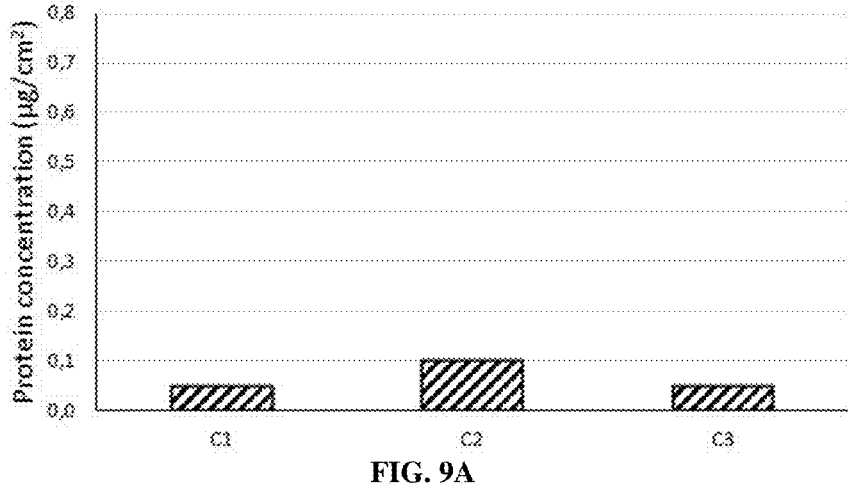
FIG. 9A shows the cleaning efficiency of the method of the disclosure for a first family of endoscopes having 3 channels.
Figure 9B:
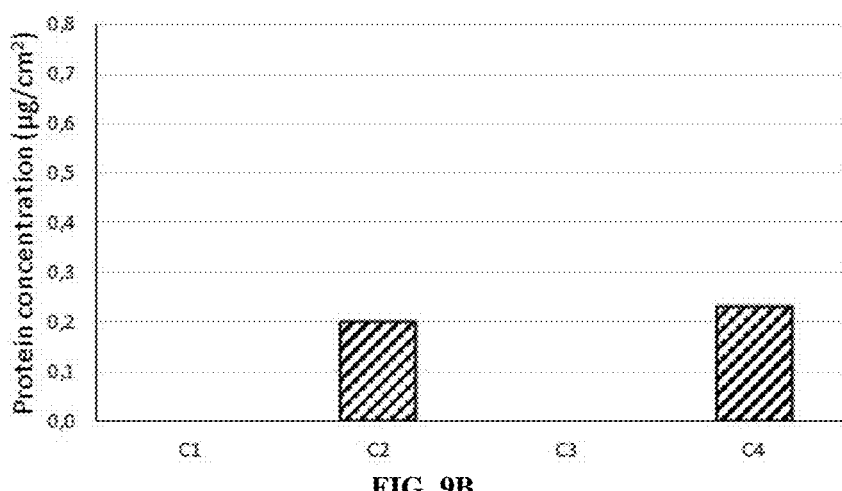
FIG. 9B shows the cleaning efficiency of the method of the disclosure for a second family of endoscopes having 4 channels.
Figure 9C:
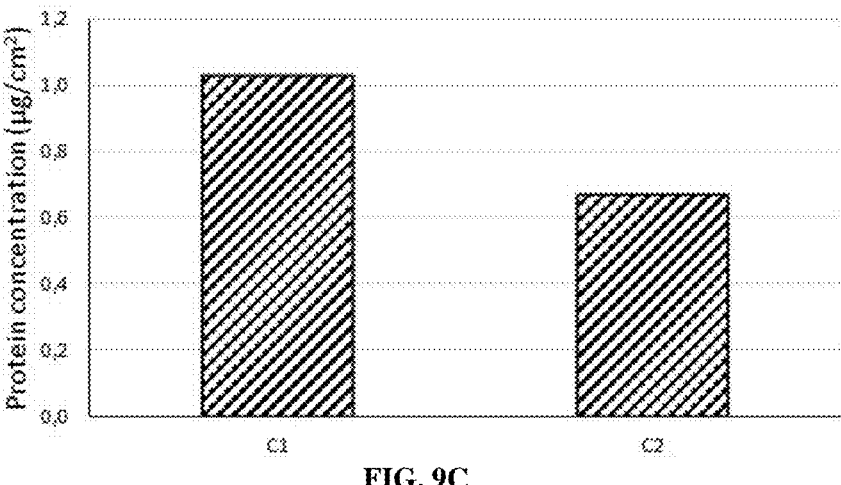
FIG. 9C shows the cleaning efficiency of the method of the disclosure for a third family of endoscopes having 2 channels.

The results are shown in FIGS. 9A, 9B and 9C representing the protein concentration in g/cm$^2$ in each of the channels of the respective family. The alert level of protein concentration at the surface of a channel is set to 3.1 μg/cm$^2$. For each family, the protein concentration is always well below the alert level after cleaning the endoscope according the method of the disclosure. The highest resulting protein concentration is for the family 3 comprising two channels. For the two other families, the resulting protein concentration is at least 10 times smaller than the alert level and is even lower than the detection limit for two of the channels of family 2.

Optional Features

Figure 6:
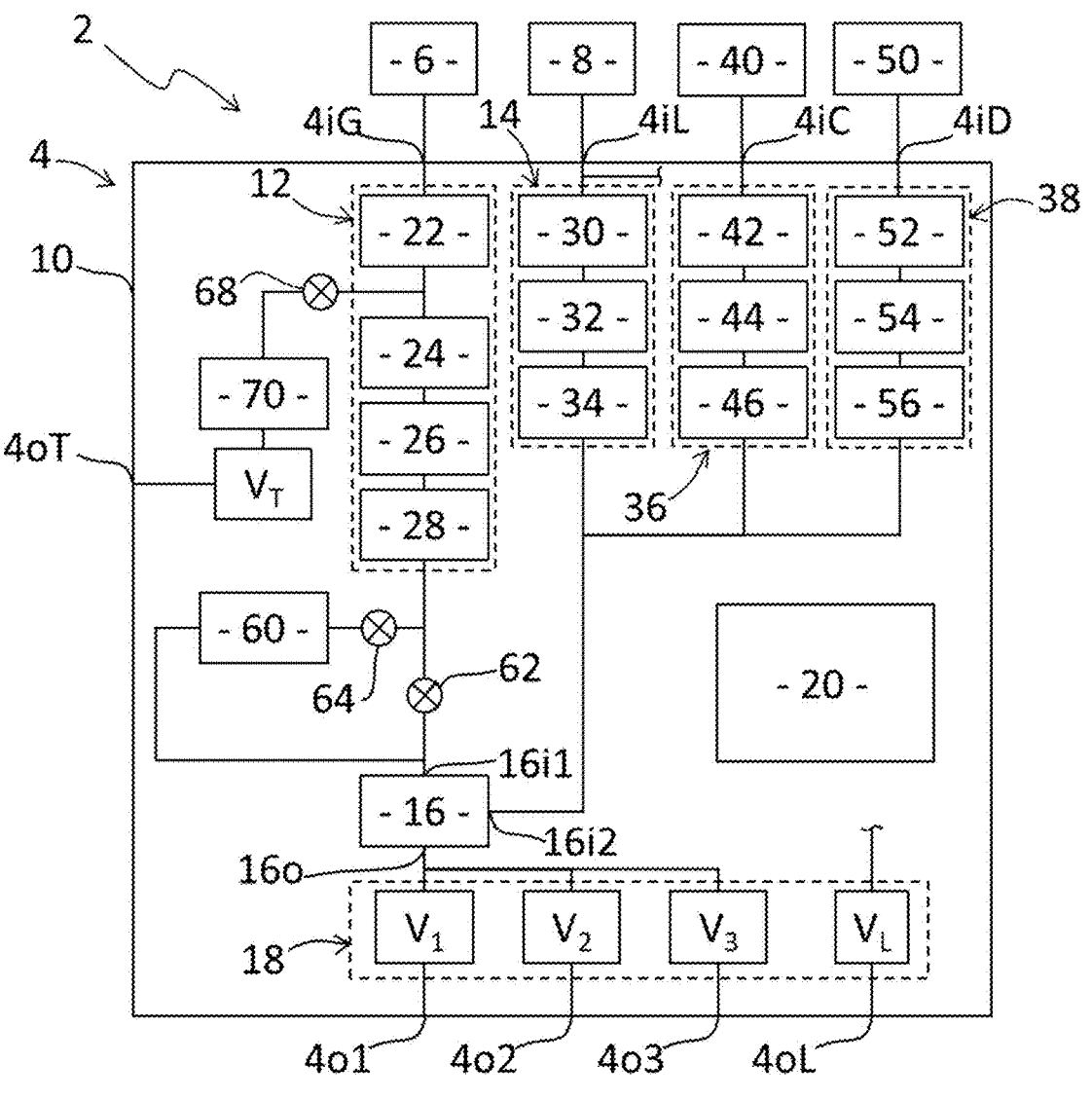
FIG. 6 is a schematic representation of a second embodiment of a cleaning assembly according to the disclosure.

According to another embodiment shown on FIG. 6, the cleaning device 4 further includes features suitable for cleaning and/or disinfecting the medical device. As a result, the cleaning device 4 is able to perform as a washer-disinfector, thereby allowing to perform contaminant removal and cleaning, as well as disinfection, using a single device. In this case, the cleaning device 4 preferably includes a basin to receive the medical device during cleaning and/or disinfection.

Cleaner Line 36

For instance, as shown on FIG. 6, the cleaning device 4 may further include an additional cleaner input 4iC and a corresponding cleaner line 36.

The cleaner input 4iC is meant to be connected to a cleaner supply 40, i.e., a supply of a cleaning solution (that is to say a detergent).

Moreover, the cleaner line 36, which is preferably controllable by the controller 20, is fluidly connected between the cleaner input 4iC and an input of the atomization chamber 16, preferably the second input 16i2.

The cleaner line 36 includes a cleaner regulator 42, a controllable valve 44 and a cleaner check valve 46 fluidly connected in series, in this order.

The cleaner regulator 42 is configured to lower the pressure of the cleaner received from the cleaner supply 40 at the cleaner input 4iC to a predetermined cleaner pressure. As a result, the cleaner regulator 42 helps protecting the remaining elements of the cleaner line 36. For instance, the predetermined cleaner pressure is between 1 bar and 4 bars.

The controllable valve 44, which can be switched between an open state and a closed state, is configured to selectively allow or prevent flowing of cleaner from the cleaner supply 40 to the atomization chamber 16, depending on controls received from the controller 20, in order to deliver a predefined amount of cleaner to the atomization chamber 16, during a respective chemical cleaning phase, which is distinct from contaminant removal phase 102. In other words, such controllable valve 44 can be placed in an open state or in a closed state to selectively allow or prevent flowing of cleaner from the cleaner supply 40 to the outlets 4o1-4oN, via the atomization chamber 16, during the chemical cleaning phase.

Furthermore, the cleaner check valve 46 is configured to prevent flow of fluids in a direction from the atomization chamber 16 to the cleaner line 36, while allowing flow of cleaner from the controllable valve 44 to the atomization chamber 16. The output of the cleaner check valve 46 is fluidly connected to the second input 16i2 of the atomization chamber 16.

Disinfectant Line 38

Furthermore, as shown on FIG. 6, the cleaning device 4 may further include an additional disinfectant input 4iD and a corresponding disinfectant line 38.

The disinfectant input 4iD is meant to be connected to a disinfectant supply 50, i.e., a supply of a disinfectant solution, such as peracetic acid.

The disinfectant line 38, which is preferably controllable by the controller 20, is fluidly connected between the disinfectant input 4iD and an input of the atomization chamber 16, preferably the second input 16i2.

The disinfectant line 38 includes a disinfectant regulator 52, a controllable valve 54 and a disinfectant check valve 56 fluidly connected in series, in this order.

The disinfectant regulator 52 is configured to lower the pressure of the disinfectant received from the disinfectant supply 50 at the disinfectant input 4iD to a predetermined disinfectant pressure. As a result, the disinfectant regulator 52 helps protecting the remaining elements of the disinfectant line 38. For instance, the predetermined disinfectant pressure is between 1 bar and 4 bars.

The controllable valve 54, which is switchable between an open state and a closed state, is configured to selectively allow or prevent flowing of disinfectant from the disinfectant supply 50 to the atomization chamber 16, depending on controls received from the controller 20, in order to deliver a predefined amount of disinfectant to the atomization chamber 16, during a respective disinfection phase, which is distinct from contaminant removal phase 102. In other words, such disinfectant valve 54 can be placed in an open state or in a closed state to selectively allow or prevent flowing of disinfectant from the disinfectant supply 50 to the outlets 4o1-4oN, via the atomization chamber 16, during the disinfection phase.

Furthermore, the disinfectant check valve 56 is configured to prevent flow of fluids in a direction from the atomization chamber 16 to the disinfectant line 38, while allowing flow of disinfectant from the controllable valve 54 to the atomization chamber 16. The output of the disinfectant check valve 56 is fluidly connected to the second input 16i2 of the atomization chamber 16.

Plasma Line

For instance, as shown on FIG. 6, the cleaning device 4 also includes a plasma line configured to generate a plasma. Preferably, such plasma is intended to be injected in a storage container meant for storing the medical device after it has been cleaned (with and/or without cleaner) and/or disinfected.

The plasma line includes a plasma chamber 60 fluidly connected in parallel to the line extending between the check valve 28 and the first input 16i1 of the atomization chamber 16.

More precisely, the plasma chamber 60 is connected in parallel with a first valve 62 located on said line extending between the check valve 28 and the first input 16i1. Furthermore, the plasma chamber 60 is connected in series with a second valve 64.

The first valve 62 and the second valve 64 are controllable (via the controller 20) so that, when one of the first valve 62 and the second valve 64 is closed, the other one of the first valve 62 and the second valve 64 is open. As a result, the flow of gas provided by the check valve 28 either goes directly to the first input 16i1 of the atomization chamber 16, or is entirely diverted through the plasma chamber 60 before reaching the first input 16i1.

The plasma chamber 60 is preferably a ceramics enclosure provided with a set of electrodes protruding in its inner cavity. In this case, the controller 20 is further configured to control a voltage supply (not shown) electrically connected to the electrodes so that a suitable voltage between said electrodes is reached when there is a need to ionize the flow of gas delivered by the check valve 28, that is to say a need to generate a plasma.

Leak Test Line

For instance, as shown on FIG. 6, the cleaning device 4 is further configured to detect leaks in a medical device, especially in an endoscope.

In this case, the cleaning device 4 further includes an additional test output 4oT and a corresponding a leak test line.

The leak test line includes a first leak valve 68, a leak regulator 70 and a second leak valve $V_T$ fluidly connected in series, in this order, between the output of the gas regulator 22 and the test output 4oT.

The leak regulator 70 is configured to lower the pressure of the gas received for the gas regulator 22 to a predetermined test pressure, typically 0.25 bars above local air pressure.

In this case, the controller 20 is preferably configured to, during a leak test phase wherein a cavity of the medical device is connected to the test output 4oT:

control valves 68 and $V_T$ to inject pressurized gas in said cavity; and measure the pressure at the test output 4oT.

Leak in this cavity results in a pressure drop over time.

More specifically, in the case of an endoscope, said cavity corresponds to a volume between the channels and the outer wall of the endoscope.

Preferably, if the pressure at the test output 4oT decreases over time, the controller 20 is configured to generate an alert signal indicating that a leak within the medical device has been detected.

The invention claimed is:

1. A cleaning method for cleaning a surface of a medical device, the method including a contaminant removal phase comprising:

a. injecting a continuous flow of gas in an atomization chamber, through a first input of the atomization chamber;

b. introducing a plurality of successive discharges of liquid in the atomization chamber through a second input of the atomization chamber, each discharge including a respective amount of liquid, a duration between two successive discharges being strictly greater than zero, thereby generating, at an output of the atomization chamber, a cleaning flow comprising, successively over time, liquid droplets suspended in gas, the cleaning flow being oriented towards the surface of the medical device.

2. The cleaning method according to claim 1, wherein b) comprises providing the plurality of successive discharges periodically, wherein the duration of each discharge is comprised between 0.1 second and 10 seconds, with a frequency comprised between 1 and 1000 discharges per minute.

3. The cleaning method according to claim 1, wherein the flow of gas at the output of the atomization chamber, during the contaminant removal phase, is turbulent.

4. The cleaning method according to claim 1, wherein, during the contaminant removal phase, a pressure of the gas, at the first input of the atomization chamber, is greater than a pressure of the liquid at the second input of the atomization chamber.

5. The cleaning method according to claim 4, wherein, during the contaminant removal phase, a concentration of surfactants in the liquid is lower than 2 mg/L.

6. The cleaning method according to claim 5, wherein a concentration of surfactants in the liquid is lower than 200 μg/L.

7. The cleaning method according to claim 5, wherein a concentration of surfactants in the liquid is lower than 100 μg/L.

8. The cleaning method according to claim 1, wherein the gas is air, dinitrogen or carbon dioxide.

9. The cleaning method according to claim 1, further including, prior to the contaminant removal phase, a preliminary phase including providing an initial flow of gas at the output of the atomization chamber, the initial flow of gas at the end of the preliminary phase being turbulent.

10. The cleaning method according to claim 1, further including, after the contaminant removal phase, a draining phase, including:

outputting, at the output of the atomization chamber, a draining flow of gas; and providing the draining flow of gas to the surface of the medical device to drain residual liquid, the draining flow of gas during the draining phase being turbulent.

11. The cleaning method according to claim 1, further including, after the contaminant removal phase, a disinfection phase comprising using a washer-disinfector to disinfect the medical device.

12. The cleaning method according to claim 1, wherein the medical device is an endoscope.

13. A cleaning device for cleaning a surface of a medical device, the cleaning device comprising:

a gas input and a liquid input, an atomization chamber including a first input, a second input and an output, a gas line fluidly connected between the gas input and the first input of the atomization chamber, a liquid line fluidly connected between the liquid input and the second input of the atomization chamber, a controller configured to control the gas line and the liquid line so that, during a phase of contaminant removal:

(a) the gas line allows circulation of gas from the gas input to the first input of the atomization chamber, in order to inject a continuous flow of gas in the atomization chamber through its first input; and (b) the liquid line allows circulation of liquid from the liquid input to the second input of the atomization chamber, in order to introduce a plurality of successive discharges of liquid in the atomization chamber through its second input, each discharge including a respective amount of liquid, a duration between two successive discharges being strictly greater than zero, thereby generating, at the output of the atomization chamber, a cleaning flow comprising, successively over time, liquid droplets suspended in gas, the cleaning flow being intended to be oriented towards the surface of the medical device.

14. The cleaning device according to claim 13, wherein the controller is configured to control the gas line so that the flow of gas at the output of the atomization chamber, during the contaminant removal phase, is turbulent.

15. The cleaning device according to claim 13, further including a set of electrodes arranged in a path of the flow of gas, the controller being configured to control a voltage between the electrodes to a level suitable for ionizing the flow of gas.

16. A cleaning assembly including a cleaning device according to claim 13, the cleaning assembly further comprising a liquid supply fluidly connected to the liquid input of the cleaning device, and a gas supply fluidly connected to the gas input of the cleaning device.

17. A washer-disinfector including a cleaning device according to claim 13.

* * * * *